United States Patent
Monna et al.

(10) Patent No.: US 10,125,657 B2
(45) Date of Patent: *Nov. 13, 2018

(54) METHOD FOR DIAGNOSING DEGRADATION OF CATALYST AND CATALYST DEGRADATION DIAGNOSIS SYSTEM

(71) Applicant: NGK INSULATORS, LTD., Nagoya-shi, Aichi (JP)

(72) Inventors: Kosuke Monna, Aichi (JP); Taku Okamoto, Nagoya (JP); Takayuki Sakurai, Kakamigahara (JP); Noriko Hirata, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 70 days.

This patent is subject to a terminal disclaimer.

(21) Appl. No.: 15/454,083

(22) Filed: Mar. 9, 2017

(65) Prior Publication Data
US 2017/0276052 A1    Sep. 28, 2017

(30) Foreign Application Priority Data
Mar. 28, 2016  (JP) ................. 2016-063366

(51) Int. Cl.
*F01N 3/08*    (2006.01)
*F01N 3/10*    (2006.01)
(Continued)

(52) U.S. Cl.
CPC .......... *F01N 11/007* (2013.01); *B01D 53/944* (2013.01); *B01D 53/9495* (2013.01);
(Continued)

(58) Field of Classification Search
CPC   B01D 53/944; G01M 15/102; G01M 15/104; F01N 3/0814; F01N 3/0835;
(Continued)

(56) References Cited

U.S. PATENT DOCUMENTS 5,296,196 A     3/1994  Takeshima
5,408,215 A *   4/1995  Hamburg ................. F01N 11/00
                                                340/439

FOREIGN PATENT DOCUMENTS

EP    1 154 131 B1   2/2005
JP    7-103039 A     4/1995
(Continued)

*Primary Examiner* — Audrey K Bradley
(74) *Attorney, Agent, or Firm* — Global IP Counselors, LLP

(57) ABSTRACT

Provided is a method for accurately diagnosing a degree of degradation of an oxidation catalyst. A target gas detecting element configured to output an electromotive force corresponding to a concentration of a target gas is provided downstream of a catalyst in an exhaust path of an internal combustion engine. A maximum change amount of an electromotive force after the introduction of a gas atmosphere for diagnosis into the catalyst is set as a diagnosis index value. The gas atmosphere has been intentionally created in the engine and includes a target gas having a concentration higher than the concentration of a target gas in a steady operation state of the engine. The index value is then compared with a threshold corresponding to the temperature of the catalyst to diagnosis whether degradation exceeding an acceptable degree has occurred in the catalyst.

8 Claims, 9 Drawing Sheets

(51) Int. Cl.
    *F01N 11/00*        (2006.01)
    *G01N 33/00*       (2006.01)
    *B01D 53/94*       (2006.01)

(52) U.S. Cl.
    CPC ......... *F01N 3/0814* (2013.01); *F01N 3/0835* (2013.01); *F01N 3/0857* (2013.01); *F01N 3/103* (2013.01); *F01N 11/00* (2013.01); *F01N 11/002* (2013.01); *G01N 33/0036* (2013.01); *F01N 2550/02* (2013.01); *F01N 2550/03* (2013.01); *F01N 2560/023* (2013.01); *F01N 2560/06* (2013.01); *F01N 2900/1402* (2013.01); *F01N 2900/1404* (2013.01); *Y02T 10/47* (2013.01)

(58) Field of Classification Search
    CPC ........ F01N 3/0857; F01N 3/103; F01N 11/00; F01N 11/007; F01N 2550/02; F01N 2550/03; F01N 2560/023; F01N 2560/06; F01N 2570/10; F01N 2570/12; F01N 2900/1402; F01N 2900/1404; Y02T 10/47
    See application file for complete search history.

(56) References Cited

FOREIGN PATENT DOCUMENTS

| | | | |
|---|---|---|---|
| JP | 08326525 A | * | 12/1996 |
| JP | 2876793 B2 | | 1/1999 |
| JP | 2001-263048 A | | 9/2001 |
| JP | 2005-240716 A | | 9/2005 |
| JP | 2012-36860 A | | 2/2012 |
| JP | 2012-241594 A | | 12/2012 |

* cited by examiner

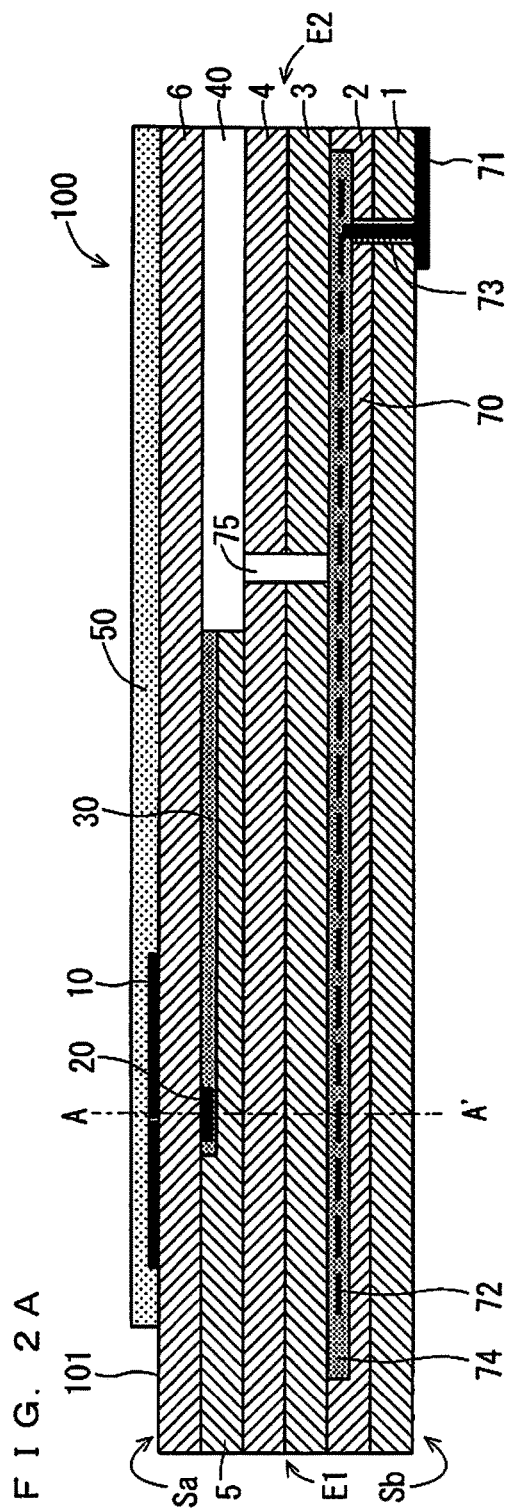
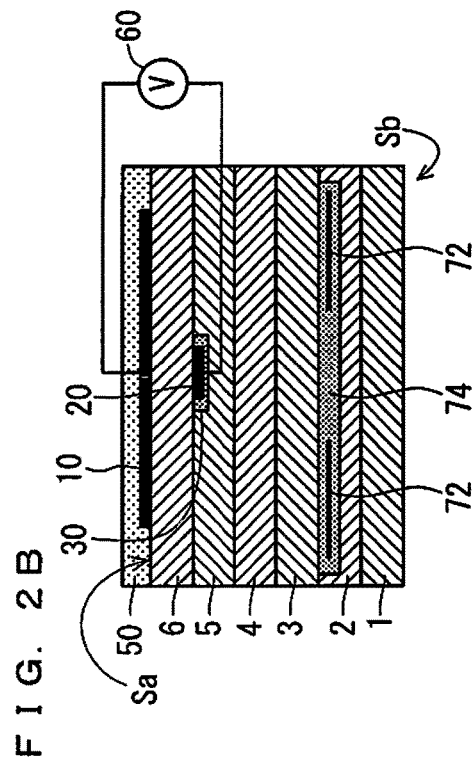
FIG. 2A
FIG. 2B

F I G. 4A
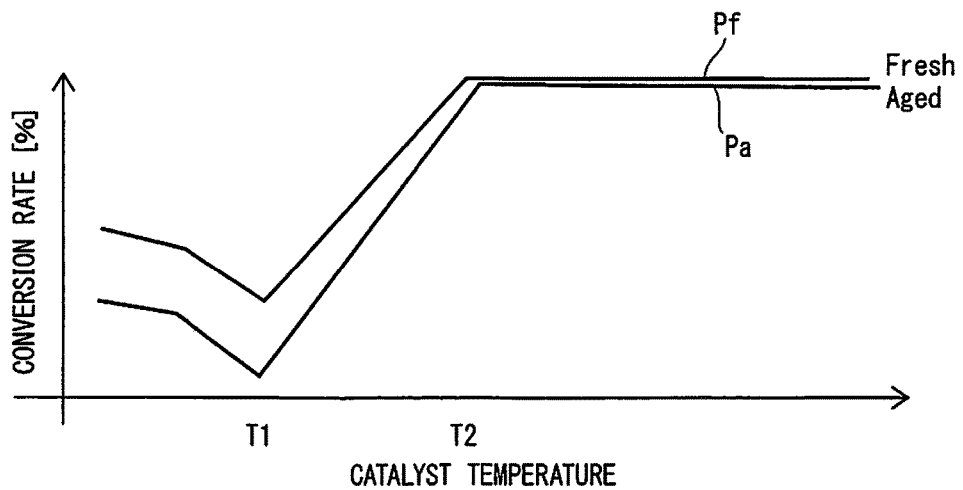
F I G. 4B
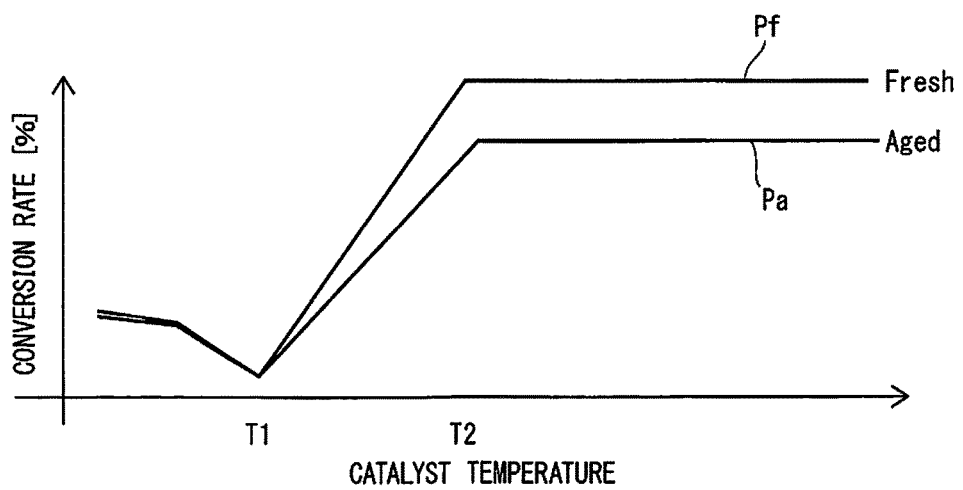

METHOD FOR DIAGNOSING DEGRADATION OF CATALYST AND CATALYST DEGRADATION DIAGNOSIS SYSTEM

BACKGROUND OF THE INVENTION

Field of the Invention

The present invention relates to a method for diagnosing a degree of degradation of a catalyst that oxidizes or adsorbs an unburned hydrocarbon gas.

Description of the Background Art

Conventionally, for on-board diagnostics (OBD) of an exhaust gas cleaning system for vehicles, that is, the function of diagnosing whether a catalyst acts normally or not in the system, a large number of patent applications have been filed mainly by auto companies. Most of these patents relate to techniques using an exhaust gas temperature sensor, oxygen sensor, wide-range oxygen concentration sensor ($\lambda$ sensor), NOx sensor, or PM sensor, and are targeted for three-way catalysts, oxidation catalysts, NOx storage catalysts, NOx selective reduction catalysts, and diesel particulate filters (DPFs) (for example, see Japanese Patent Application Laid-Open Nos. 2001-263048, 2005-240716, 2012-036860, 2012-241594, and 07-103039 (1995)).

Various types of hydrocarbon gas sensors (HC sensors) for measuring vehicle exhaust gases based on various principles have been researched and developed. A HC sensor of semiconductor type that is applicable to control of purification for NOx in a zeolite catalyst and is capable of selectively detecting a hydrocarbon (HC) having a large molecular weight is publicly known (for example, see Japanese Patent No. 2876793). HC sensors of various types have been widely known, such as catalytic combustion gas sensors, oxygen-concentration difference sensing gas sensors, limiting current gas sensors, and mixed-potential gas sensors, for which a large number of patent applications have been filed peaking around the year 2000.

Such HC sensors are, however, assumed mainly to be used in an inspection of the purification performance of exhaust gas purification devices (three-way catalyst (TWC), NOx storage catalyst (NSC)) mounted in a gasoline engine of a theoretical equivalent ratio (air excess ratio $\lambda=1$) combustion type or a lean-burn ($\lambda>1$) type, or used in control of injection amount for an unburned hydrocarbon in a diesel engine.

Entering the 2010s, regulations on exhaust gases have been tightened in the North America, and especially, OBD of oxidation catalysts for diesel engine vehicles will be made mandatory in the future. Specifically, oxidation catalysts for diesel engines have been required to undergo OBD targeted for nom methane hydro carbon (NMHC) in an excessive oxygen ($O_2$) atmosphere that is an exhaust atmosphere of a diesel engine.

However, the publicly known techniques involving the use of sensors, as disclosed in Japanese Patent Application Laid-Open Nos. 2001-263048, 2005-240716, 2012-036860, 2012-241594, and 07-103039, cannot support such OBD or can only make an indirect diagnosis.

For example, disclosed in Japanese Patent Application Laid-Open No. 2001-263048 is a technique involving the use of a relationship that when the ability of converting (oxidizing or combusting) an unburned hydrocarbon in an oxidation catalyst decreases, exothermic energy will also decrease. In outline, a temperature difference AT is measured, which occurs at the time of fuel injection in exhaust gas temperature sensors disposed forward and reward (upstream and downstream) of an oxidation catalyst in an exhaust path, and the degree of degradation in the ability of converting (oxidizing or combusting) an unburned hydrocarbon in the oxidation catalyst is diagnosed indirectly from a measurement value.

In this method, however, a cause of error may be excessively large due to changes in the temperature and the flow rate of an exhaust gas when the gas sensors are practically used, and fuel consumption may inevitably degrade because a large amount of fuel injection is required for accelerating heat generation.

Disclosed in Japanese Patent Application Laid-Open No. 2005-240716 is a technique involving the use of a fact that when the ability of converting an unburned hydrocarbon in an oxidation catalyst decreases, the amount of oxygen consumed during the combustion of oxygen changes. In outline, on the basis of a difference $\Delta\lambda$ between output values $\lambda F$ and $\lambda R$ of two wide-range oxygen concentration sensors ($\lambda$ sensors) disposed forward and reward of an oxidation catalyst in an exhaust path, or a difference between output values (electromotive force values) of two oxygen sensors, an amount of oxygen consumed in an oxidation catalyst is measured, and the degree of degradation in the ability of converting an unburned hydrocarbon on the oxidation catalyst is diagnosed indirectly from a change in the measured value.

However, the concentration of oxygen in a diesel exhaust that is an excessive $O_2$ atmosphere is approximately 10% (=100000 ppm), whereas the amount (concentration) of hydrocarbon that is converted (oxidized or combusted) by an oxidation catalyst is normally on the order of several hundreds of ppm, and the amount (concentration) of oxygen consumed when such a trace amount of hydrocarbon is burned is no more than several hundreds of ppm. This means that the diagnosis of the degradation of an oxidation catalyst with an air-fuel ratio sensor or oxygen sensor requires an accurate calculation of $\Delta\lambda$ or a difference in electromotive force corresponding to a ppm-order change in the amount of oxygen consumed, but the air-fuel sensors and oxygen sensors originally cannot achieve such accuracy in measurements.

Disclosed in Japanese Patent Application Laid-Open No.2012-036860 is a technique for disposing a NOx sensor downstream of an oxidation catalyst that oxidizes NO into $NO_2$ in an exhaust path and determining a degree of degradation of the oxidation catalyst on the basis of a predetermined map and an output value (electromotive force value) of the NOx sensor.

However, even if such a technique can diagnose the ability of oxidizing NO of an oxidation catalyst, the result of this diagnosis cannot be applied to diagnosis of the ability of converting (oxidizing or combusting) an unburned hydrocarbon. This is because the functions of a precious metal catalyst and a storage agent vary for the types of gases (e.g., HC, CO, NO), and accordingly, the relationship between the temperature of an exhaust gas and a conversion (oxidization or combustion) rate also differs in the respective gases, and no specific correlation is found therebetween.

Additionally, because an estimated value is used as a NOx value for the exhaust immediately after a discharge of an engine or factors except for an engine speed and an engine load are not taken into account in setting of such an estimated value, it is conceivable that the accuracy of estimation will degrade remarkably depending on usage condition.

Disclosed in Japanese Patent Application Laid-Open No. 2012-241594 is a method for disposing an exhaust gas temperature sensor and a λ sensor forward and reward of an oxidation catalyst and diagnosing a degree of degradation of the oxidation catalyst on the basis of an amount of required oxygen obtained from an estimated value of a HC storage capability during a normal activity of the oxidation catalyst and an estimated value of an amount of oxygen actually consumed, which is an amount of oxygen actually consumed by the oxidation catalyst.

Such a technique, however, merely makes a diagnosis based on an estimated value, and is inevitably affected by errors of signals from the respective sensors, leading to low diagnosis accuracy.

Disclosed in Japanese Patent Application Laid-Open No. 07-103039 is a system whose diagnosis target is a TWC or NSC of a gasoline engine. Japanese Patent Application Laid-Open No. 07-103039 discloses nothing about the diagnosis of an oxidation catalyst in diesel exhaust that is an excessive $O_2$ state.

SUMMARY OF THE INVENTION

The present invention relates to a method for diagnosing a degree of degradation of a catalyst that oxidizes or adsorbs an unburned hydrocarbon gas. In particular, the present invention relates to the diagnosis of degradation of a catalyst that is provided in an exhaust path of an internal combustion engine and oxides or adsorbs a target gas including at least one of a hydrocarbon gas and a carbon monoxide gas contained in an exhaust gas from the internal combustion engine.

According to the present invention, a method for diagnosing a degree of degradation of a catalyst, in which the catalyst is provided in an exhaust path of an internal combustion engine and oxidizes or adsorbs a target gas including at least one of a hydrocarbon gas and a carbon monoxide gas contained in an exhaust gas from the internal combustion engine, includes (a) providing a target gas detecting element downstream of the catalyst in the exhaust path, the target gas detecting element being configured to output an electromotive force corresponding to a concentration of the target gas as a detection signal of the target gas, and (b) comparing a diagnosis index value with a threshold to diagnose whether degradation exceeding an acceptable degree has occurred in the catalyst. The diagnosis index value is a maximum change amount of the electromotive force after introduction of a gas atmosphere for diagnosis into the catalyst for a predetermined period of time. The gas atmosphere for diagnosis includes a target gas having a concentration higher than the concentration of the target gas during a steady operation state of the internal combustion engine. The target gas is intentionally generated in the internal combustion engine. The threshold is set corresponding to a temperature of the catalyst determined at a timing at which the gas atmosphere for diagnosis is introduced According to the present invention, a degree of degradation in the catalytic ability in the oxidation catalyst can be diagnosed in real time with good accuracy without calculation of a conversion rate that is an index of the catalytic ability and without the influences of a nitrogen monoxide gas and a nitrogen dioxide gas that are interference gases with an unburned hydrocarbon gas.

Preferably, the step (b) in the method according to the present invention includes (b-1) measuring a temperature of the exhaust gas containing the target gas upstream of the catalyst in the exhaust path in response to an execution instruction to make a degradation diagnosis of the catalyst, the execution instruction being issued at an appropriate timing during the steady operation state of the internal combustion engine, (b-2) subsequent to the measuring of the temperature of the exhaust gas in the step (b-1), injecting a fuel from the internal combustion engine to generate a gas for diagnosis, (b-3) identifying the diagnosis index value on the basis of a time-variable profile of the electromotive force from a start to an end of exhaust of the gas for diagnosis from the catalyst, and (b-4) diagnosing a degree of degradation in the catalyst on the basis of the diagnosis index value and a value of the threshold determined regarding the temperature of the exhaust gas measured in the step (b-1) as the temperature of the catalyst. In the step (b-4), a diagnosis is made that degradation exceeding the acceptable degree has not occurred in the catalyst if the diagnosis index value identified in the step (b-3) is smaller than or equal to the threshold, and a diagnosis is made that degradation exceeding the acceptable degree has occurred in the catalyst if the diagnosis index value identified in the step (b-3) is greater than the threshold.

The present invention therefore has an object to provide a method for accurately diagnosing a degree of degradation of an oxidation catalyst.

BRIEF DESCRIPTION OF THE DRAWINGS

FIGS. 2A and 2B are schematic sectional views of an example configuration of a HC sensor 100;

FIGS. 4A and 4B schematically illustrate another example of a conversion rate profile Pa;

DESCRIPTION OF THE PREFERRED EMBODIMENTS

Overview of System

Figure 1:
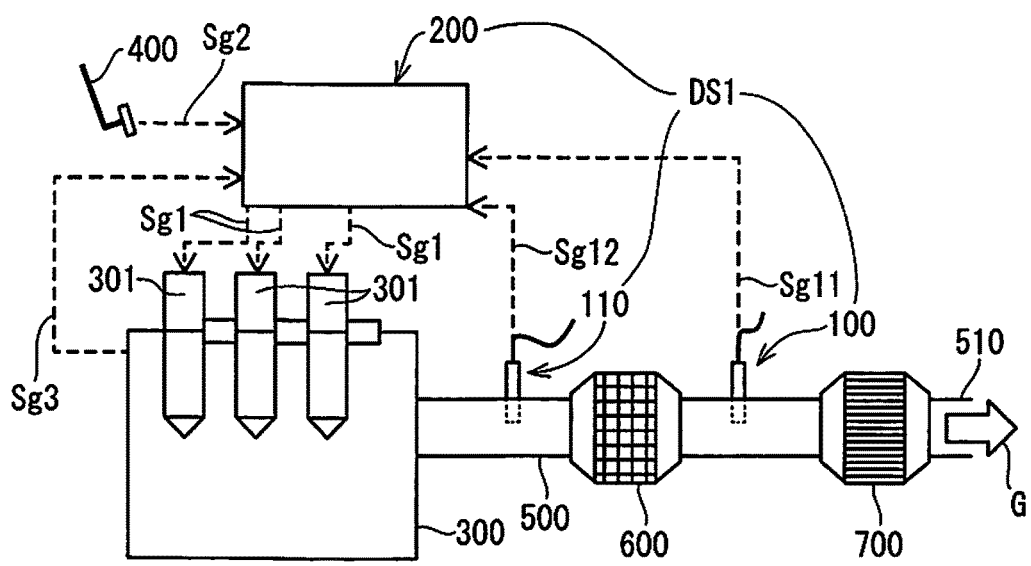
FIG. 1 schematically illustrates a configuration of a diesel engine system 1000 including an oxidation catalyst diagnosis system DS1.

FIG. 1 schematically illustrates a configuration of a diesel engine system (hereinafter also merely referred to as an engine system) 1000 including an oxidation catalyst diagnosis system DS1 according to an embodiment of the present invention.

The oxidation catalyst diagnosis system DS1 mainly includes a hydrocarbon gas sensor (hereinafter also referred to as a HC sensor) 100, a temperature sensor 110, and an electronic controller 200 that is a controller for controlling an operation of the entire engine system 1000.

The engine system 1000 includes, in addition to the oxidation catalyst diagnosis system DS1, an engine main body 300 that is a diesel engine of one type of internal combustion engine, a plurality of fuel injection valves 301 that inject a fuel into the engine main body 300, a fuel injection instruction part 400 for instructing the fuel injection valves 301 to inject a fuel, an exhaust pipe 500 forming an exhaust path that externally discharges an exhaust gas (engine exhaust) G generated in the engine main body 300, and an oxidation catalyst 600 such as platinum or palladium that is provided at some midpoint of the exhaust pipe 500 and oxidizes or adsorbs an unburned hydrocarbon gas in the exhaust gas G. In the present embodiment, in a relative meaning, the position closer to the engine main body 300 that is one side of the exhaust pipe 500 is referred to an upstream side, and the position closer to an exhaust port 510 that is opposite the engine main body 300 is referred to as a downstream side.

The engine system 1000 is typically mounted in a vehicle, and in such a case, the fuel injection instruction part 400 is an accelerator pedal.

In the engine system 1000, the electronic controller 200 issues a fuel injection instruction signal sg1 to the fuel injection valves 301. The fuel injection instruction signal sg1 is usually issued in response to a fuel injection request signal sg2 for demanding an injection of a predetermined amount of fuel, which is provided from the fuel injection instruction part 400 to the electronic controller 200 during the operation (action) of the engine system 1000 (e.g., an accelerator pedal is depressed so that an optimum fuel injection reflecting a large number of parameters, such as the position of an accelerator, an amount of oxygen intake, an engine speed, and torque is demanded). In addition to this, a fuel injection instruction signal sg1 may be issued for the oxidation catalyst diagnosis system DS1 to operate.

A monitor signal sg3 for monitoring various situations inside the engine main body 300 is provided from the engine main body 300 to the electronic controller 200.

In the engine system 1000, the exhaust gas G exhausted from the engine main body 300 that is a diesel engine is a gas in an excessive oxygen ($O_2$) atmosphere having an oxygen concentration of approximately 10%. Specifically, such an exhaust gas G contains oxygen and unburned hydrocarbon gas, and also contains nitrogen oxide, soot (graphite), and the like. In this specification, an unburned hydrocarbon gas that is a gas (target gas) targeted for the adsorption or oxidation process in the oxidation catalyst 600 contains not only typical hydrocarbon gases (classified as hydrocarbons by a chemical formula) such as $C_2H_4$, $C_3H_6$, and n-C8, but also carbon monoxide (CO). The HC sensor 100 can preferably detect a target gas, including CO. However, $CH_4$ is excluded.

The engine system 1000 may include one or a plurality of purification devices 700 at some midpoint of the exhaust pipe 500, in addition to the oxidation catalyst 600.

The oxidation catalyst diagnosis system DS1 is targeted for a diagnosis of a degree of degradation of the oxidation catalyst 600 (more specifically, a degree of degradation in the catalytic ability of the oxidation catalyst 600). The oxidation catalyst 600 is provided to adsorb or oxide an unburned hydrocarbon gas in the exhaust gas G that has flowed from the upstream side to prevent the unburned hydrocarbon gas from flowing out through the exhaust port 510 at the end of the exhaust pipe 500, but its catalytic ability (specifically, adsorbing capability and oxidizing capability) degrades with time. The occurrence of such degradation is not preferable because it increases an amount of an unburned hydrocarbon gas that is not captured by the oxidation catalyst 600 but flows downstream. The oxidation catalyst diagnosis system DS1 according to the present embodiment detects the unburned hydrocarbon gas that has passed through the oxidation catalyst 600 with the HC sensor 100 to diagnose the degree of degradation in the catalytic ability of the oxidation catalyst 600.

The oxidation catalyst diagnosis system DS1 includes the HC sensor 100 and the temperature sensor 110 as described above. The former is disposed downstream of the oxidation catalyst 600 in the exhaust pipe 500 and detects the concentration of an unburned hydrocarbon gas in the relevant portion, and the latter is disposed upstream of the oxidation catalyst 600 and detects the temperature (exhaust temperature) of the exhaust gas G in the relevant portion. The HC sensor 100 and the temperature sensor 110 are each disposed such that one end thereof is inserted into the exhaust pipe 500.

In outline, in the oxidation catalyst diagnosis system DS1, the electronic controller 200 is configured to diagnose whether the oxidation catalyst 600 has degraded or not on the basis of a HC detection signal sg11 issued from the HC sensor 100 and an exhaust temperature detection signal sg12 issued from the temperature sensor 110. The example configuration of the HC sensor 100 and the details of diagnosis of degradation will be described below. The temperature sensor 110 may be a conventionally known sensor as one used to measure an exhaust temperature in a common engine system.

The electronic controller 200 includes storage (not shown) such as memory or HDD, and the storage stores a program for controlling the operations of the engine system 1000 and the oxidation catalyst diagnosis system DS1, and also stores threshold data used to diagnose the degree of degradation of the oxidation catalyst 600 described below.

Example Configuration of HC Sensor

FIGS. 2A and 2B are schematic sectional views of an example configuration of the HC sensor 100 used in the present embodiment. FIG. 2A is a vertical sectional view of a sensor element 101, which is a main component of the HC sensor 100, taken along the longitudinal direction of the sensor element 101. FIG. 2B is a view including a cross-section of the sensor element 101 perpendicular to the longitudinal direction of the sensor element 101 at a position A-A' of FIG. 2A.

The HC sensor 100 used in the present embodiment is a so-called mixed-potential gas sensor. Generally speaking, the HC sensor 100 determines the concentration of a gas component, which is a measurement target, of a measurement gas using a potential difference that occurs between a sensing electrode 10, which is provided on the surface of the sensor element 101 mainly made of ceramic that is an oxygen-ion conductive solid electrolyte such as zirconia ($ZrO_2$), and a reference electrode 20, which is provided inside the sensor element 101, due to a difference in the concentration of the gas component between the portions near the electrodes on the basis of the principle of mixed potential.

In the presence of a plurality of unburned hydrocarbon gases in a measurement gas, a potential difference occurring between the sensing electrode 10 and the reference electrode 20 is a value reflecting all the unburned hydrocarbon gases, and thus, a concentration value to be determined is also a total sum of the concentrations of the plurality of unburned hydrocarbon gases.

The sensor element 101 mainly includes a reference gas introduction layer 30, a reference gas introduction space 40, and a surface protective layer 50 in addition to the sensing electrode 10 and the reference electrode 20 described above.

In the present embodiment, the sensor element 101 has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 2A and 2B. The sensor element 101 additionally includes other components mainly between these layers or on an outer peripheral surface of the element. The solid electrolytes constituting these six layers are fully airtight. Such a sensor element 101 is manufactured by, for example, laminating ceramic green sheets corresponding to the individual layers, which have been subjected to a predetermined process and printing of a circuit pattern, and further, by integrating the laminated layers through firing.

In the following description, for the sake of convenience, the surface located as the upper surface of the sixth solid electrolyte layer 6 in FIGS. 2A and 2B is referred to as a front surface Sa of the sensor element 101, and the surface located as the lower surface of the first solid electrolyte layer 1 in FIGS. 2A and 2B is referred to as a rear surface Sb of the sensor element 101. In the determination of the concentration of the unburned hydrocarbon gas in a measurement gas with the HC sensor 100, a predetermined range starting from a distal end E1 being one end of the sensor element 101, which includes at least the sensing electrode 10, is disposed in a measurement gas atmosphere, and the other portion including a base end E2 opposite the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101 on the front surface Sa.

The catalytic activity of the sensing electrode 10 against an unburned hydrocarbon gas is disabled by preferably determining the composition of the Pt—Au alloy being its constituent material. That is, the decomposition reaction of an unburned hydrocarbon gas is prevented or reduced in the sensing electrode 10. In the HC sensor 100, accordingly, the potential of the sensing electrode 10 selectively varies with respect to (has correlation with) the unburned hydrocarbon gas, in accordance with its concentration. In other words, the sensing electrode 10 is provided so as to have high dependence of potential on concentration for an unburned hydrocarbon gas while having low dependence of potential on concentration for any other component of the measurement gas. This is achieved by gold (Au), in addition to platinum (Pt) that is a main component, being contained as a conductive component (noble metal component) of the sensing electrode 10.

Specifically, the sensing electrode 10 is formed such that the ratio of Au (Au abundance ratio) in the sensing electrode 10 is 0.3 or more. As a result of the formation of the sensing electrode 10 in such a manner, the detection sensitivity of the HC sensor 100 is increased more than in the case where the sensing electrode 10 is formed as a cermet electrode of Pt and zirconia similarly to the reference electrode 20. In the HC sensor 100, accordingly, also when an unburned hydrocarbon gas contained in an exhaust gas G in an excessive oxygen atmosphere generated in the engine main body 300 as described above is a detection target, the unburned hydrocarbon gas can be detected with good detection sensitivity.

In this specification, the Au abundance ratio means an area ratio of the portion covered with Au to the portion at which Pt is exposed in the surface of the noble metal particle of the sensing electrode 10. The Au abundance ratio is 1 when the area of the portion at which Pt is exposed is equal to the area of the portion covered with Au. In this specification, a Au abundance ratio is calculated from a peak intensity of a peak detected for Au and Pt, obtained using X-ray photoelectron spectroscopy (XPS), by a relative sensitivity coefficient method.

When the Au abundance ratio is 0.3 or more, in the sensing electrode 10, Au is enriched in the surface of a noble metal particle of the sensing electrode 10. More specifically, a Au-rich Pt—Au alloy is formed near the surface of a Pt-rich Pt—Au alloy particle. When such a state is achieved, the catalytic activity in the sensing electrode 10 is disabled preferably, and the dependence of the potential of the sensing electrode 10 on the concentration of unburned hydrocarbon gas is enhanced.

It suffices that the volume ratio between a noble metal component and zirconia of the sensing electrode 10 is approximately from 5:5 to 8:2.

For the HC sensor 100 to preferably exhibit its function, the porosity of the sensing electrode 10 is preferably 10% or more and 30% or less, and the thickness of the sensing electrode 10 is preferably 5 μm or more. In particular, the porosity is more preferably 15% or more and 25% or less, and the thickness is more preferably 25 μm or more and 45 μm or less.

The plane size of the sensing electrode 10 may be determined appropriately, and it suffices that, for example, the length in the longitudinal direction of the sensor element is approximately 0.2 mm to 10 mm and the length perpendicular to the longitudinal direction is approximately 1 mm to 5 mm.

The reference electrode 20 is an electrode having a substantially rectangular shape in plan view, which is provided inside the sensor element 101 and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 μm or more and 15 μm or less. The plane size of the reference electrode 20 may be smaller than that of the sensing electrode 10 as illustrated in FIGS. 2A and 2B, or may be equal to that of the sensing electrode 10.

The reference gas introduction layer 30 is a layer made of porous alumina, which is provided inside the sensor element 101 to cover the reference electrode 20. The reference gas introduction space 40 is an internal space provided on the base end E2 of the sensor element 101. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the HC sensor 100, the surrounding of the reference electrode 20 is always filled with air (oxygen) through the reference gas introduction space 40 and the reference gas introduction layer 30. During the use of the HC sensor 100, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even if the sensing electrode 10 is exposed to the measurement gas.

In the case illustrated in FIG. 2A, the reference gas introduction space 40 is provided in such a manner that part of the fifth solid electrolyte layer 5 is in communication with the exterior on the base end E2 of the sensor element 101. The reference gas introduction layer 30 is provided so as to extend in the longitudinal direction of the sensor element 101 between the fifth solid electrolyte layer 5 and the sixth solid electrolyte layer 6. The reference electrode 20 is provided under the center of gravity of the sensing electrode 10 with reference to FIGS. 2A and 2B.

The surface protective layer 50 is a porous layer made of alumina, which is provided so as to cover at least the sensing electrode 10 on the front surface Sa of the sensor element 101. The surface protective layer 50 is provided as an electrode protective layer that prevents or reduces the degradation of the sensing electrode 10 due to continuous exposure to a measurement gas during the use of the HC sensor 100. In the case illustrated in FIG. 2A, the surface protective layer 50 is provided so as to cover not only the sensing electrode 10 but also substantially the entire front surface Sa of the sensor element 101 except for a predetermined range starting from the distal end E1.

As illustrated in FIG. 2B, the HC sensor 100 is equipped with a potentiometer 60 capable of measuring a potential difference between the sensing electrode 10 and the reference electrode 20. Although FIG. 2B schematically illustrates wiring between the potentiometer 60 and each of the sensing electrode 10 and the reference electrode 20, in an actual sensor element 101, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. In the present embodiment, a potential difference between the sensing electrode 10 and the reference electrode 20, which is measured by the potentiometer 60, is a detection signal sgl1. This potential difference is also referred to as a HC sensor output.

The sensor element 101 further includes a heater part 70, which performs temperature control of heating the sensor element 101 and maintaining the temperature of the sensor element 101, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101 (in FIGS. 2A and 2B, the lower surface of the first solid electrolyte layer 1). The heater part 70 can be powered externally through the heater electrode 71 connected with an external power supply (not shown).

The heater 72 is an electric resistor provided inside the sensor element 101. The heater 72 is connected with the heater electrode 71 through the through hole 73 and generates heat by being powered externally via the heater electrode 71 to heat the solid electrolytes forming the sensor element 101 and maintain their temperatures.

In the case illustrated in FIGS. 2A and 2B, the heater 72 is buried while being vertically sandwiched between the second solid electrolyte layer 2 and the third solid electrolyte layer 3 so as to extend from the base end E2 to the position below the sensing electrode 10 near the distal end E1. This enables the adjustment of the entire sensor element 101 to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and to be in communication with the reference gas introduction space 40, and is formed to mitigate an internal pressure rise associated with a temperature rise in the heater insulating layer 74.

In the determination of the concentration of an unburned hydrocarbon gas in the exhaust gas G from the engine main body 300, which is a measurement gas, using the HC sensor 100 having the above configuration, as described above, air (oxygen) is supplied to the reference gas introduction space 40, with the sensor element 101 in only a predetermined range, which starts from the distal end E1 and includes at least the sensing electrode 10, being disposed in the exhaust pipe 500 of the engine system 1000, and with the sensor element 101 on the base end E2 being apart from the space. The heater 72 heats the sensor element 101 to an appropriate temperature from 300° C. to 800° C., preferably from 400° C. to 700° C., more preferably from 400° C. to 600° C.

In such a state, a potential difference occurs between the sensing electrode 10 exposed to the measurement gas (exhaust gas G) and the reference electrode 20 disposed in the air atmosphere. As described above, however, the potential of the reference electrode 20 disposed in the air (having a constant oxygen concentration) atmosphere is maintained at a constant, whereas the potential of the sensing electrode 10 selectively has a dependence on concentration for the unburned hydrocarbon gas of the measurement gas (exhaust gas G). The potential difference (HC sensor output) is thus substantially a value according to the concentration of the measurement gas present around the sensing electrode 10. Therefore, a certain functional relationship (referred to as sensitivity characteristics) holds between the concentration of the unburned hydrocarbon gas and the sensor output. Such sensitivity characteristics can be used to determine the concentration of the unburned hydrocarbon gas in the measurement gas.

That is to say, a plurality of different mixed gases, each of which has a known concentration of an unburned hydrocarbon gas, are prepared as the measurement gases in advance, and the sensor output for each measurement gas is measured, thereby experimentally identifying sensitivity characteristics. Then, these sensitivity characteristics are stored in the electronic controller 200. The electronic controller 200 converts the sensor output, which varies momentarily in accordance with the concentration of an unburned hydrocarbon gas in a measurement gas, into the concentration of the unburned hydrocarbon gas on the basis of the sensitivity characteristics. The concentration of the unburned hydrocarbon gas downstream of the oxidation catalyst 600 can thus be determined almost in real time.

In the present embodiment, further, changes in the HC sensor output value (potential difference value) that is provided as the HC detection signal sgl1 is used for degradation diagnosis, which will be described below.

Characteristics of Oxidation Catalyst

Description will now be given of the characteristics of the oxidation catalyst 600 that is a target of a degradation diagnosis by the oxidation catalyst diagnosis system DS1 according to the present embodiment.

Figure 3:
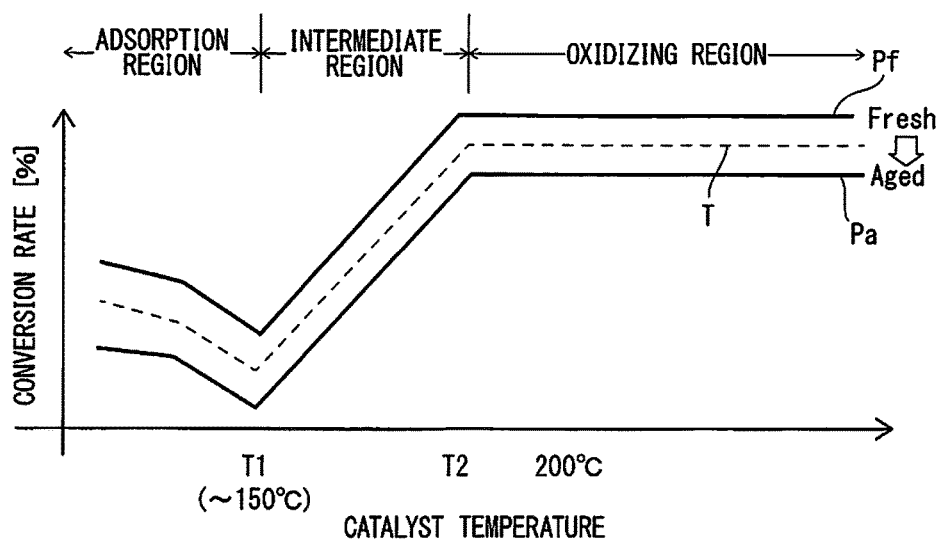
FIG. 3 schematically illustrates a relationship between a temperature and a conversion rate of an oxidation catalyst 600.

FIG. 3 schematically illustrates a relationship (conversion rate profile) between a temperature (catalyst temperature) and a conversion rate of the oxidation catalyst 600. FIG. 3 schematically illustrates a conversion rate profile Pf of an oxidation catalyst 600 (also referred to as a fresh product or merely "fresh") at an initial stage of use (unused or immediately after use) and a conversion rate profile Pa of an oxidation catalyst 600 (also referred to as an aged product or merely "aged") after use for a certain period.

The conversion rate is a value serving as an index of the catalytic ability in the oxidation catalyst 600, and is defined by Expression 1 below, where the concentration of an unburned hydrocarbon gas in the neighborhood of the upstream side of the oxidation catalyst 600 is represented as an upstream unburned hydrocarbon gas concentration Nu and the concentration of an unburned hydrocarbon gas in the neighborhood of the downstream side of the oxidation catalyst 600 is represented as a downstream unburned hydrocarbon gas concentration Nl.

$$\text{Conversion Rate (\%)} = 100 \times (Nu - Nl)/Nu \quad \text{(Expression 1)}$$

That is to say, the conversion rate represents a ratio of the unburned hydrocarbon gas that has not flowed downstream from the oxidation catalyst 600 with respect to the unburned hydrocarbon that has flowed into the oxidation catalyst 600 from the upstream side. This means that an oxidation catalyst 600 having a higher conversion rate has better catalytic ability.

More specifically, the oxidation catalyst 600 has an action of exclusively adsorbing an unburned hydrocarbon gas (adsorbing capability) in a temperature range (an adsorption region in FIG. 3) of a temperature T1 (approximately 150° C.) or lower temperature, and preferably exhibits the ability of oxidizing an unburned hydrocarbon gas (oxidizing capability), which is its original function, in a temperature range (an oxidizing region in FIG. 3) of a temperature T2 (normally between 150° C. and 200° C.) or higher temperature. In a temperature range between the temperature T1 and the temperature T2 (an intermediate region in FIG. 3), the adsorbing capability decreases and the oxidizing capability increases as the temperature rises. The conversion rate is therefore a value indicating a percentage at which the unburned hydrocarbon gas that has flowed from the upstream side into the oxidation catalyst 600 is adsorbed or oxidized in the oxidation catalyst 600.

As illustrated in FIG. 3, the conversion rate profile Pf of the fresh product normally has the highest conversion rate (approximately 90%) in the oxidizing region and has a conversion rate lower in the adsorption region than in the oxidizing region. Moreover, the conversion rate tends to be at its minimum in the upper limit temperature T1 (approximately 150° C.) of the adsorption region and become higher as the temperature rises in the intermediate region.

However, the temperature of the oxidation catalyst 600 can vary momentarily depending on the temperature (exhaust temperature) of the exhaust gas G that is discharged from the engine main body 300 and flows through the exhaust pipe 500 into the oxidation catalyst 600, and accordingly, an actual conversion rate also varies momentarily.

The oxidation catalyst 600 that has a high conversion rate when it is a fresh product will also eventually degrade after a continuous use. That is to say, the conversion rate of the oxidation catalyst 600 will decrease irrespective of temperature as it reaches an aged product after a continuous use. Although the conversion rate profile Pa of the aged product has approximately the same magnitude relationship of the conversion rate between in the adsorption region and the oxidizing region as the conversion rate profile Pf of the fresh product, it has a conversion rate lower than that of the conversion rate profile Pf at the same temperature.

Overview of Degradation Diagnosis

If a conversion rate decreases below a predetermined level as a result of a continuous use of the oxidation catalyst 600 as described above, the oxidation catalyst 600 cannot exhibit its originally intended function. For example, in the case that the engine system 1000 is mounted in a vehicle, some malfunctions such that the vehicle will not satisfy environmental criteria may occur. The oxidation catalyst diagnosis system DS1 according to the present embodiment diagnoses, on the basis of predetermined criteria, whether degradation to such a degree that it is regarded as a problem (e.g., replacement is required) has occurred in the oxidation catalyst 600 that is an aged product, thereby enabling timely replacement of the oxidation catalyst 600 from an aged product to a fresh product in the engine system 1000.

Conceptually, data (threshold data) corresponding to a threshold profile T in which a threshold of conversion rate is determined per temperature, as illustrated in FIG. 3, is prepared in advance and is stored in the electronic controller 200 of the oxidation catalyst diagnosis system DS1. And then, the temperature and conversion rate of the oxidation catalyst 600 that is a diagnosis target are determined. Consequently, it can be diagnosed that the oxidation catalyst 600 has degraded if the obtained conversion rate is lower than the threshold at the temperature.

The conversion rate profile Pa of the aged product illustrated in FIG. 3 takes values smaller than those of the conversion rate profile Pf by approximately a constant value at all the temperatures, which is merely an example. FIGS. 4A and 4B schematically illustrate alternative examples of the conversion rate profile Pa. That is to say, the conversion rate profile Pa of an aged product may degrade to a larger degree in the adsorption region than in the oxidizing region as illustrated in FIG. 4A, or conversely, degrade to a larger degree in the oxidizing region than in the adsorption region as illustrated in FIG. 4B. It is therefore preferable that the degradation that has occurred in the temperature range of the temperature T1 or lower temperature be detected timely in the case illustrated in FIG. 4A and that the degradation that has occurred in the temperature range of the temperature T2 or higher temperature be detected timely in the case illustrated in FIG. 4B.

In the present embodiment, a degree of degradation of the oxidation catalyst 600 is diagnosed on the basis of a change amount ($\Delta$EMF) of an electromotive force value (EMF) that is an output value (HC detection signal sgl1) in the HC sensor 100 provided downstream of the oxidation catalyst 600. On that occasion, a so-called active on-board diagnostics (OBD) technique is employed, in which a trace amount of fuel is intentionally injected for a short period of time during the operation of the engine main body 300 to generate a hydrocarbon gas for diagnosis, and the resultant hydrocarbon gas atmosphere for diagnosis is targeted in diagnosing. That is to say, a change amount of the output value in the HC sensor 100 in an intentional fuel injection is used to diagnose the degradation of the oxidation catalyst 600.

The hydrocarbon gas atmosphere used in an active OBD diagnosis is obtained by superimposing the hydrocarbon gas for diagnosis on an unburned hydrocarbon gas contained in a normal exhaust gas G. Note that in the following description, for the sake of convenience, the hydrocarbon gas for diagnosis may also be referred to as an unburned hydrocarbon gas.

Figure 5:
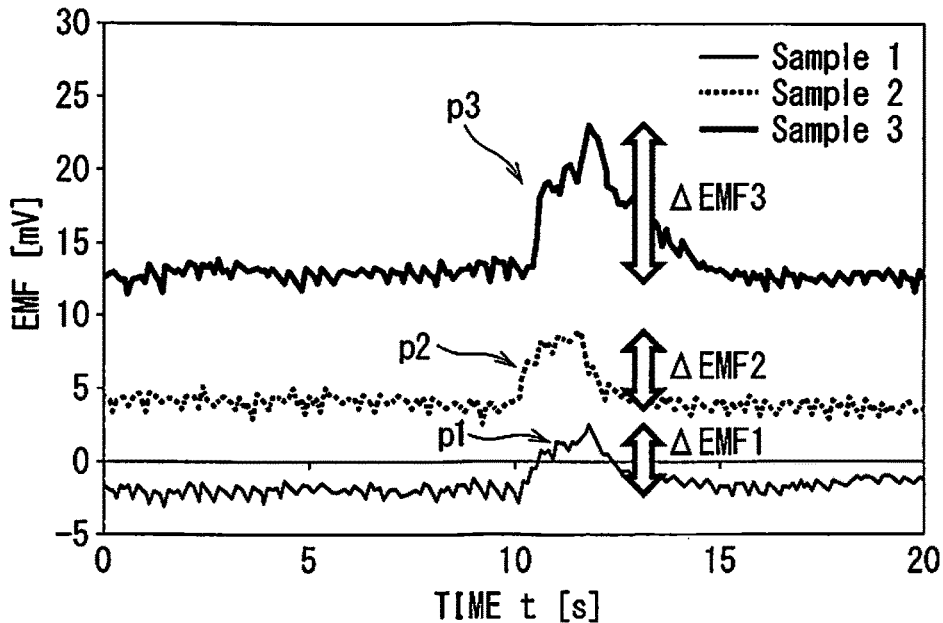
FIG. 5 illustrates time-variable profiles of EMF in the HC sensor 100 for three types of oxidation catalysts.
Figure 6:
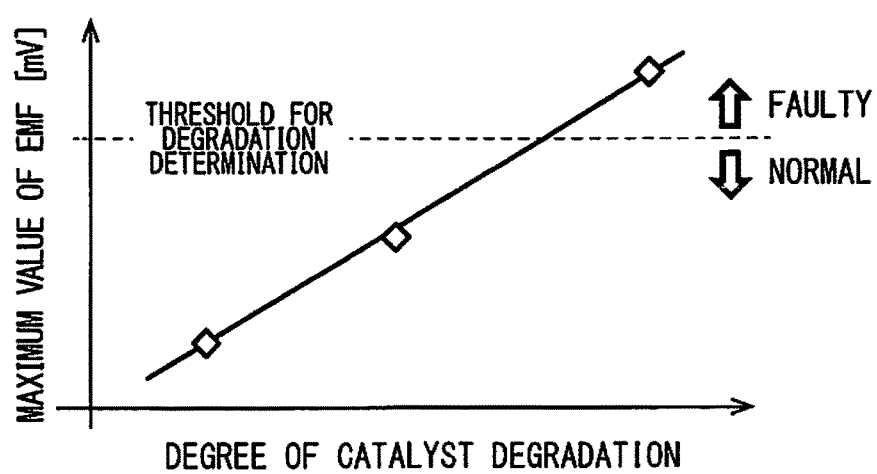
FIG. 6 conceptually illustrates a degradation diagnosis made in an embodiment.

FIG. 5 illustrates time-variable profiles of EMF (hereinafter, merely referred to as electromotive force profiles) in the HC sensors 100 included in the respective oxidation catalyst diagnosis systems DS1. These profiles are obtained when three types of oxidation catalysts 600, which may degrade to different degrees because they have been used in different situations after manufacture on the same conditions, are installed in the engine system 1000 and a fuel is injected for a short period of time on the same injection conditions at a catalyst temperature set at 400° C. The three oxidation catalysts 600 included in the engine systems 1000 will be referred to as Sample 1, Sample 2, and Sample 3. FIG. 6 conceptually illustrates a degradation diagnosis made in the present embodiment.

As illustrated in FIG. 5, in all the electromotive force profiles of Sample 1, Sample 2, and Sample 3, peaks p1, p2, and p3 corresponding to the respective fuel injections appear past near t=10. These are peaks resulting from an unburned hydrocarbon gas in the fuel that has not been fully oxidized in the oxidation catalyst 600 and has been discharged downstream. The magnitudes of these peaks p1, p2, and p3 thus reflect the conversion rates of the respective oxidation catalysts 600, that is, catalytic abilities. This is because the oxidation catalyst 600 that is almost a fresh product has a higher conversion rate, and accordingly, an unburned hydrocarbon gas introduced into the oxidation catalyst 600 through fuel injection is discharged downstream at a lower rate; the oxidation catalyst 600 that has been used and become an aged product has a lower conversion rate, and accordingly, an unburned hydrocarbon gas introduced into the oxidation catalyst 600 through fuel injection is discharged downstream at a higher rate.

In the case illustrated in FIG. 5, peak intensities (maximum values of a change amount ΔEMF of EMF from a baseline) ΔEMF1 and ΔEMF2 of the peaks p1 and p2 for Samples 1 and 2 are similar to each other; a peak intensity ≠EMF3 of the peak p3 for Sample 3 is higher than ΔEMF1 and ΔEMF2. This means that the degradation of the oxidation catalyst 600 of Sample 3 has progressed more than the oxidation catalysts 600 of Samples 1 and 2.

As described above, the maximum value (hereinafter also referred to as a maximum change amount) of ΔEMF correlates with the degree of the degradation of the oxidation catalyst 600. In the present embodiment, thus, a maximum change amount is regarded as an index value of a degradation diagnosis (diagnosis index value), and as illustrated in FIG. 6, a determination is made that the oxidation catalyst 600 is normal if the maximum change amount is equal to or smaller than a predetermined threshold (in FIG. 6, "threshold for degradation determination"), whereas a determination is made that the degradation of the oxidation catalyst 600 has progressed to such a degree that the oxidation catalyst 600 needs to be replaced (in FIG. 6, such a situation is referred to as "faulty") if the maximum change amount exceeds the threshold.

More specifically, the catalytic ability of the oxidation catalyst 600 differs depending on temperature as illustrated in FIGS. 3, 4A, and 4B. The threshold of the maximum change amount is therefore determined in advance in accordance with the temperature that the oxidation catalyst 600 can reach and is stored in the storage of the electronic controller 200. The maximum change amount of ΔEMF increases as a fuel injection amount increases, and accordingly, the fuel injection conditions in degradation diagnosis are preferably set constant.

Although the example illustrated in FIG. 5 is targeted for the temperature of the oxidation catalyst 600 in the oxidizing region, a diagnosis can be made by a similar technique at the temperature of the oxidation catalyst 600 in the adsorption region. Even when the conversion rate of the oxidation catalyst 600 decreases to a different degree depending on temperature as illustrated in FIGS. 4A and 4B, a reliable diagnosis can be achieved.

Since the three electromotive force profiles illustrated in FIG. 5 have totally different values of baselines themselves, it seems that at first glance, the degree of degradation can be diagnosed on the basis of the magnitude relationship of the baselines themselves, that is, with the use of values of the baselines as diagnosis index values. This is because in a situation in which the exhaust gas G containing an unburned hydrocarbon flows steadily, the conversion rate of the oxidation catalyst 600 gradually decreases after continuous use, and it is accordingly conceivable that the EMF value will increase along with such a decrease.

However, the diagnosis of the degree of degradation with the use of the value of the base line as a diagnosis index value may fail to always yield an accurate result, so it is not preferred. This is because even at the same concentration of a hydrocarbon gas, an electromotive force obtained in the HC sensor 100 may vary due to the influences of NO (nitrogen monoxide) and $NO_2$ (nitrogen dioxide) that are interference gases with a hydrocarbon gas.

Figure 7:
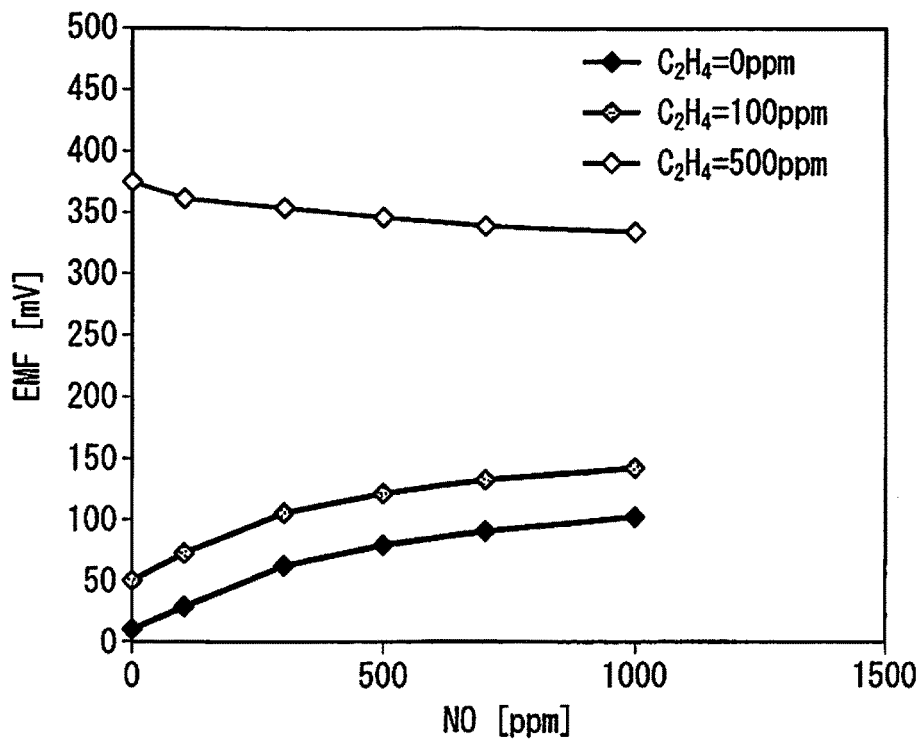
FIG. 7 illustrates how an EMF value varies in the HC sensor 100 due to the influence of NO.
Figure 8:
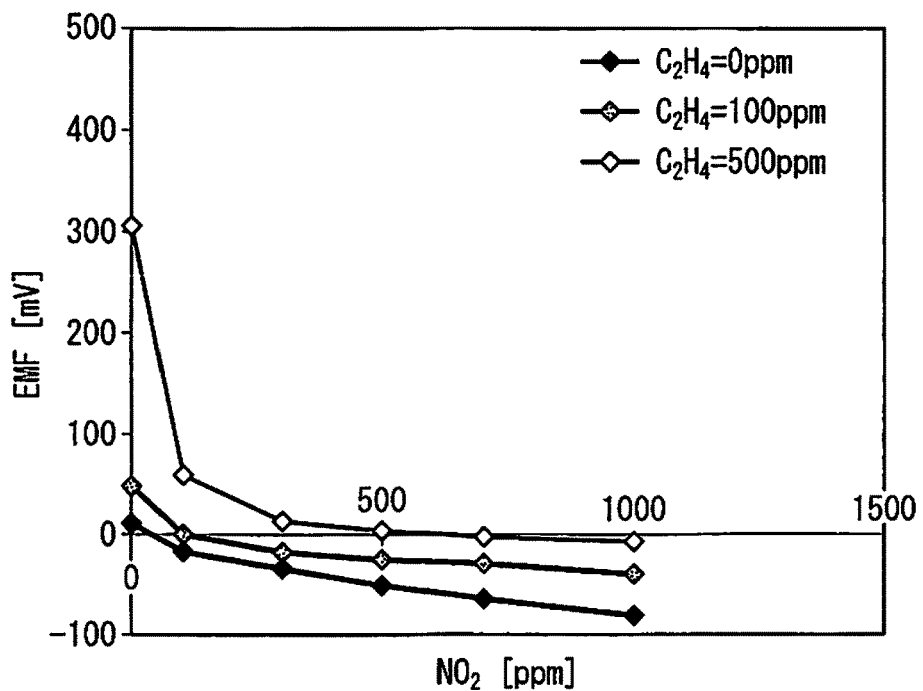
FIG. 8 illustrates how an EMF value varies in the HC sensor 100 due to the influence of $NO_2$.

FIGS. 7 and 8 illustrate how the EMF value in the HC sensor 100 varies due to the influences of NO (nitrogen monoxide) and $NO_2$ (nitrogen dioxide). FIGS. 7 and 8 illustrate electromotive force (EMF), which is generated when the HC sensor 100 is placed in a mixed gas atmosphere, plotted against the NO concentration or $NO_2$ concentration. The mixed gas atmosphere is obtained by adding a NO gas (in the case of FIG. 7) or a $NO_2$ gas (in the case of FIG. 8) while changing its concentration on a hydrocarbon gas (specifically, ethylene, $C_2H_4$) having a constant concentration. The concentration of the hydrocarbon gas is varied in three levels, 0 ppm, 100 ppm, and 500 ppm, and the concentrations of the NO gas and the $NO_2$ gas are varied in six levels, 0 ppm, 100 ppm, 300 ppm, 500 ppm, 700 ppm, and 1000 ppm.

Although the EMF value originally should be the same due to a constant concentration of a hydrocarbon gas, as illustrated in FIGS. 7 and 8, the EMF value varies in accordance with the concentration of NO and the concentration of $NO_2$. These results indicate that a degradation diagnosis is not always preferably made with the use of the values of the baselines of the electromotive force profiles obtained as exemplarily illustrated in FIG. 5 as diagnosis index values.

In contrast, when a peak appearing in an electromotive force profile is used for degradation diagnosis with the use of the active OBD technique as in the present embodiment, the electromotive force clearly changes correspondingly to the degree of degradation of the oxidation catalyst 600 in the HC sensor 100. Consequently, whether the oxidation catalyst 600 has degraded to such a degree that requires replacement can be diagnosed reliably.

If a conversion rate is calculated on the basis of Expression 1, the concentration of an unburned hydrocarbon gas needs to be determined upstream as well as downstream of the oxidation catalyst 600. In contrast, the oxidation catalyst diagnosis system DS1 according to the present embodiment uses a value of ΔEMF in the HC sensor 100 disposed downstream of the oxidation catalyst 600 as described above, and is accordingly advantageous in that no HC sensor needs to be provided upstream of the oxidation catalyst 600.

The active OBD in which a fuel is injected intentionally seems to be disadvantageous at first glance in terms of securing fuel mileage in the engine system 1000. However, a total amount of fuel injection performed in the oxidation catalyst diagnosis system DS1 according to the present embodiment is much smaller than in a fuel injection performed for another purpose in the engine system 1000 or in a fuel injection when another diagnostic technique is employed, whose influence on fuel mileage is kept at a minimum.

Specifically, a fuel injection in active OBD is performed at a timing of a post-injection in the engine cycle of the engine main body 300. A unit injection amount is preferably 0.5 to 10 (mg/injection), an injection time is preferably 0.01 to 3 (sec), and a total injection amount is preferably 0.002 to 10 (g). In such a case, a diagnosis based on active OBD can be preferably made while minimizing a fuel injection amount. The total injection amount is calculated by Expression 2 below.

Total Injection Amount (g)=Unit Injection Amount (mg/injection)×Injection Time (sec)×Engine Speed (rpm)×Number of Cylinders/(60×2×1000)  (Expression 2)

For example, at an engine speed of 1600 (rpm) in an in-line-4 engine, a total injection amount is 0.224 (g) if a unit injection amount is 3 (mg/injection) and an injection time is 1.4 (sec).

For comparison, when a fuel injection (diesel particulate filter (DPF) regeneration mode) for regenerating the DPF, which is performed for the DPF normally mounted in an exhaust pipe of a vehicle, is performed at an engine speed of 2000 (rpm) at which the exhaust temperature reaches approximately 150° C., an injection with a unit injection amount of approximately 6 (mg/injection) is performed for an injection time of approximately 150 (sec). In such a case, the total injection amount of the in-line-4 engine is approximately 60 (g). This value is several hundreds of times the total injection amount with which a diagnosis based on active OBD is made in the present embodiment, and thus, the fuel consumption in active OBD performed in the present embodiment is practically very small.

Example of Diagnosis Procedure

Figure 9:
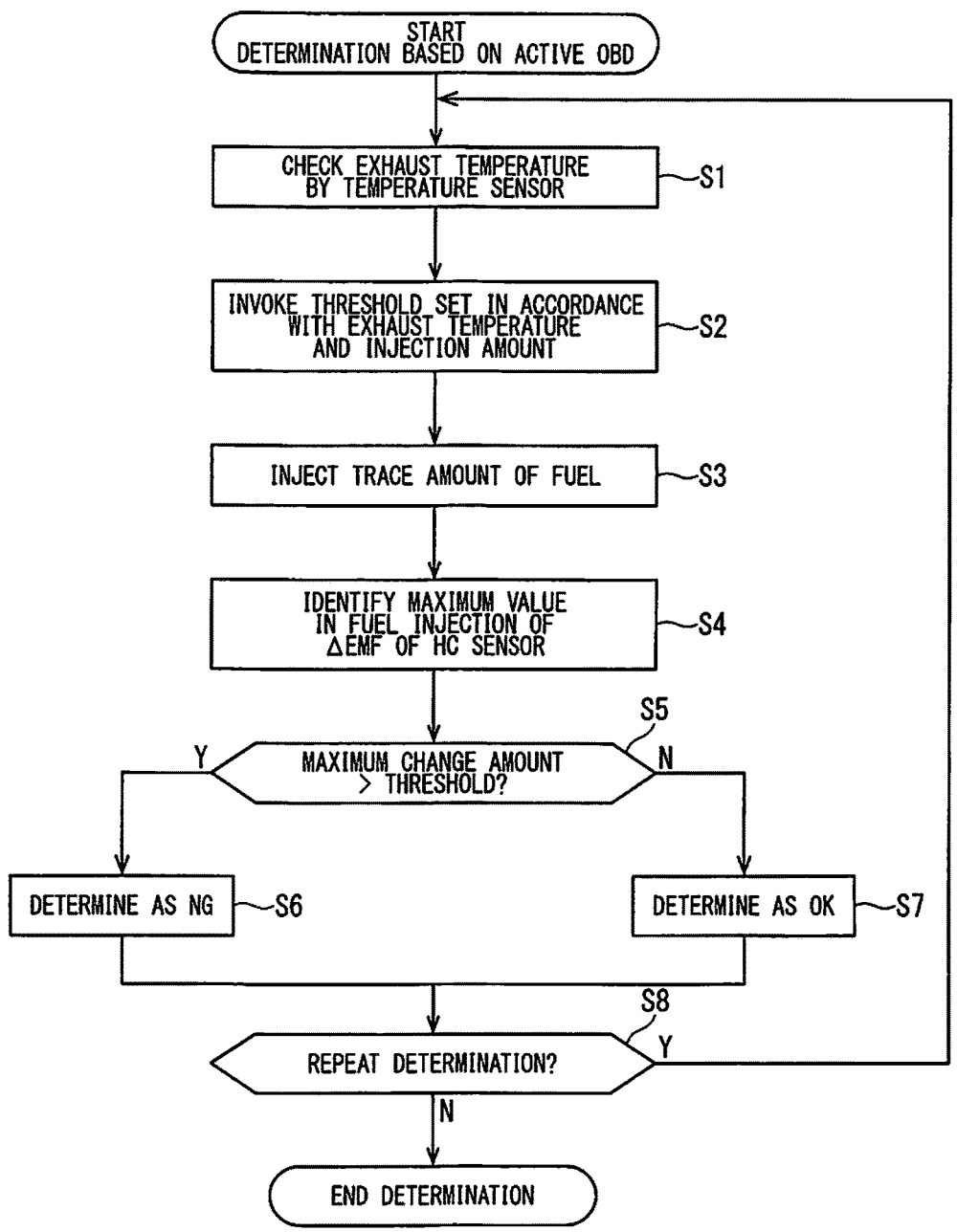
FIG. 9 illustrates an example procedure of a degradation diagnosis made in an embodiment.

FIG. 9 illustrates an example procedure of a degradation diagnosis made in the present embodiment. The degradation diagnosis in the present embodiment starts first by the temperature sensor 110 checking the temperature (exhaust temperature) of an exhaust gas G in the neighborhood of the upstream side of the oxidation catalyst 600 (step S1). In more detail, an exhaust temperature is identified by the electronic controller 200 obtaining an exhaust temperature detection signal sg12 issued from the temperature sensor 110. Such an exhaust temperature is regarded as the temperature of the oxidation catalyst 600 at that point of time.

Subsequently, the electronic controller 200 invokes a threshold of an unburned hydrocarbon gas concentration corresponding to the exhaust temperature from the threshold data stored in advance in the storage of the electronic controller 200 (step S2). The threshold is determined in advance at all the temperatures within the temperature range (approximately −40° C. to 1000° C.) that the oxidation catalyst 600 can reach. There is no specific limitation on how to provide a threshold, and accordingly, the threshold may be provided as a continuous function of the temperature (exhaust temperature) of the oxidation catalyst 600 or may be provided as a fixed value per temperature range.

Subsequently, the electronic controller 200 issues a fuel injection instruction signal sg1 to the fuel injection valves 301 to generate a trace amount of fuel injection for a short period of time from the fuel injection valves 301 (step S3). As described above, such a fuel injection is performed at a timing of a post-injection in the engine cycle of the engine main body 300.

After the fuel injection, in addition to the exhaust gas G steadily discharged along with the operation of the engine main body 300, the injected fuel is vaporized inside the engine main body 300 and is discharged to the exhaust pipe 500 in a superimposed manner, so that an unburned hydrocarbon gas having a higher concentration than in the constant operation is delivered to the oxidation catalyst 600.

Then, at a timing linked to such a fuel injection, a maximum value (maximum change amount) of a change amount (ΔEMF) of the electromotive force (EMF) in the HC sensor 100 during a fuel injection is identified (step S4).

Figure 10:
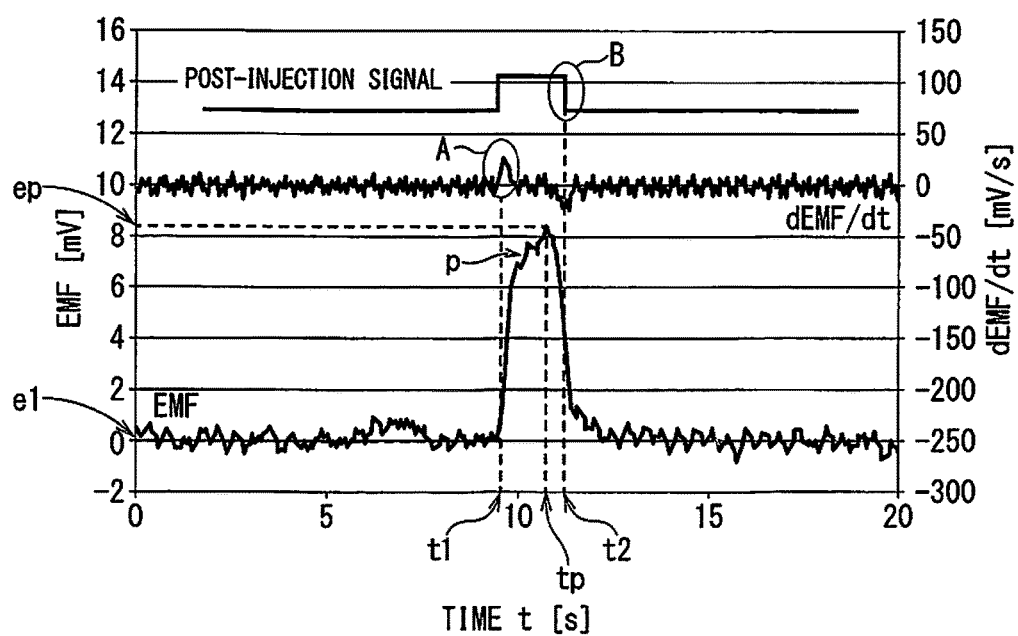
FIG. 10 illustrates a specific technique for identifying a maximum change amount of ΔEMF.

FIG. 10 illustrates a specific technique for identifying a maximum change amount of ΔEMF. As indicated by a "post-injection signal" in FIG. 10, a fuel injection in a degradation diagnosis is made only for a predetermined period of time, that is, in a so-called pulsed manner. As a result of such a fuel injection, a peak p appears in an electromotive force profile indicated by "EMF" in FIG. 10.

Since a peak p appears in the manner described above, the value of dEMF/dt that is a time differential value of EMF, which remains almost constant in a steady state, increases instantaneously at a timing of a fuel injection. The electronic controller 200 constantly monitors the value of dEMF/dt and regards a time t1 (timing A in FIG. 10) at which the value of dEMF/dt is equal to or greater than a predetermined threshold as a time at which a peak p starts to appear (peak formation start time) in the electromotive force profile. The electronic controller 200 regards a time t2 (timing B in FIG. 10) at which a fuel injection ends as a time at which the formation of the peak p ends (peak formation end time).

Between the times t1 to t2, a maximum value of ΔEMF is identified on the basis of the value e1 of EMF at the time t1. In the case illustrated in FIG. 10, a difference value ep-e1 between values ep at the time tp and e1 of EMF is identified as a maximum change amount of ΔEMF for the peak p, that is, a diagnosis index value.

After a maximum change amount of ΔEMF is identified and a threshold is invoked in such a manner, the electronic controller 200 compares the maximum change amount of ΔEMF, which is a diagnosis index value, with the threshold (step S5). The electronic controller 200 then diagnoses that degradation to such a degree that it is regarded as a problem (e.g., replacement is required) has occurred in the oxidation catalyst 600 (NG) (step S6) if the maximum change amount is greater (YES in step S5), or if the threshold is greater (NO in step S5), diagnoses that the above-mentioned degradation has not occurred in the oxidation catalyst 600 (OK) (step S7).

If a diagnosis is repeated after the former diagnosis completes irrespective of whether a diagnosis has been made as NG or OK (YES in step S8), the process is repeated again from the check of an exhaust temperature by the temperature sensor 110 (NO in step S8).

As described above, the oxidation catalyst diagnosis system according to the present embodiment diagnoses a degree of degradation in the catalytic ability in an oxidation catalyst, which is provided at some midpoint of the exhaust pipe from the engine main body being a diesel engine in the engine system and oxidizes or adsorbs an unburned hydrocarbon gas in an exhaust gas, by intentionally increasing the concentration of an unburned hydrocarbon gas that flows into the oxidation catalyst through injection of a trace amount of fuel and then determining a change in the electromotive force corresponding to the concentration of the unburned hydrocarbon gas at a position in the neighborhood of the downstream side of the oxidation catalyst in the exhaust pipe, which has been directly measured by the hydrocarbon gas sensor located at this position. This enables a diagnosis in real time with good accuracy without calculating a conversion rate that is an index of the catalytic ability.

In particular, degradation is diagnosed on the basis of the maximum change amount of an electromotive force, and thus, the diagnosis can be made with good accuracy without being affected by a nitrogen monoxide gas and a nitrogen dioxide gas that are interference gases with the unburned hydrocarbon gas.

Oxidation catalysts 600 having different conversion rates that have been manufactured in the same conditions were prepared, and maximum change amounts of ΔEMF were evaluated for the respective electromotive force profiles while varying a catalyst temperature and fuel injection conditions. Specifically, oxidation catalysts 600 having conversion rates of 75%, 78%, and 83% were prepared, and the catalyst temperature was varied in three levels, 300° C., 350° C., and 400° C. As to the fuel injection conditions, at an engine speed of 1600 (rpm) of an in-line-4 engine, the unit injection amount was varied in two levels, 3 (mg/injection) and 5 (mg/injection), and an injection time was kept constant at 1.4 (sec). Total injection amounts in the respective conditions were 0.224 (g) and 0.373 (g).

Figure 11A:
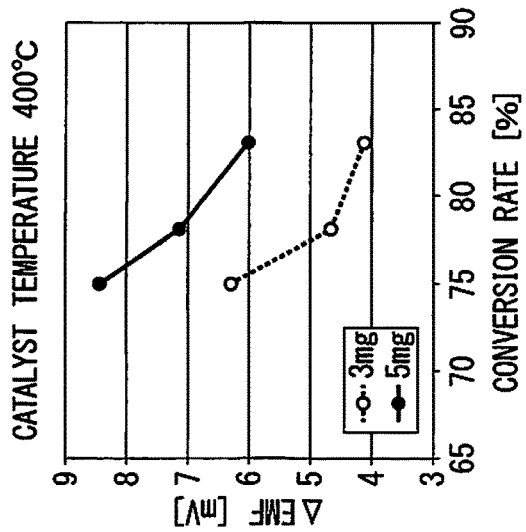
FIGS. 11A, 11B, and 11C are each a plot of a maximum change amount of ΔEMF against a conversion rate for each catalyst temperature and for each fuel injection condition.
Figure 11B:
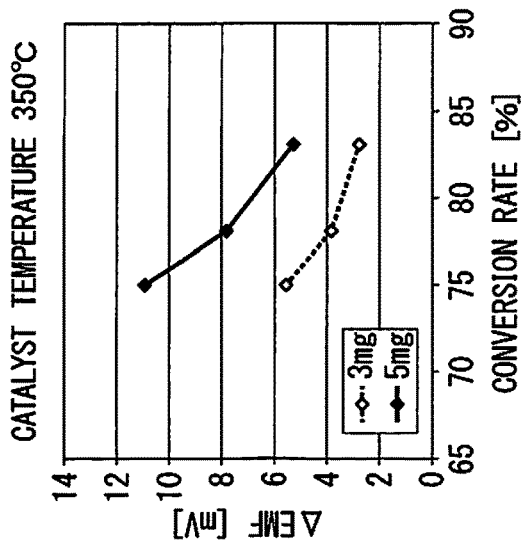
Figure 11C:
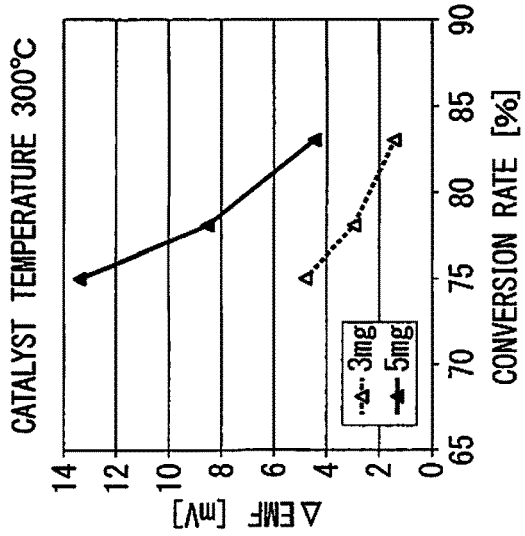

FIGS. 11A, 11B, and 11C are each a plot of a maximum change amount of ΔEMF (in FIGS. 11A, 11B, and 11C, merely described as ΔEMF) against a conversion rate for each catalyst temperature and for each fuel injection condition. FIGS. 11A, 11B, and 11C respectively illustrate the results at the catalyst temperatures of 300° C., 350° C., and 400° C.

FIGS. 11A, 11B, and 11C reveal that there is a correlation between a conversion rate and a maximum change amount of ΔEMF at any catalyst temperature. Such results indicate that, at least in the range of 300° C. or a higher temperature that is a normal use temperature range of the oxidation catalyst 600, degradation of the oxidation catalyst 600 can be diagnosed with the use of the maximum change amount of ΔEMF as a diagnosis index value, and that a conversion rate can be monitored (a conversion rate can be estimated) on the basis of the maximum change amount of ΔEMF.

What is claimed is:

1. A method for diagnosing a degree of degradation of a catalyst, said catalyst being provided in an exhaust path of an internal combustion engine and oxidizing or adsorbing a target gas including at least one of a hydrocarbon gas and a carbon monoxide gas contained in an exhaust gas from said internal combustion engine,
the method comprising:
(a) providing a target gas detecting element downstream of said catalyst in said exhaust path, said target gas detecting element being configured to output an electromotive force corresponding to a concentration of said target gas as a detection signal of said target gas; and (b) comparing a diagnosis index value with a threshold to diagnose whether degradation exceeding an acceptable degree has occurred in said catalyst, said diagnosis index value being a maximum change amount of said electromotive force after introduction of a gas atmosphere for diagnosis into said catalyst for a predetermined period of time, said gas atmosphere for diagnosis including a target gas having a concentration higher than the concentration of said target gas during a steady operation state of said internal combustion engine, said target gas being intentionally generated in said internal combustion engine, and said threshold being set corresponding to a temperature of said catalyst determined at a timing at which said gas atmosphere for diagnosis is introduced.

2. The method according to claim 1, wherein a mixed-potential hydrocarbon gas sensor is used as said target gas detecting element, said hydrocarbon gas sensor including a sensing electrode made of a Pt—Au alloy to disable a catalytic activity in said sensing electrode.

3. The method according to claim 1, wherein said step (b) includes
(b-1) measuring a temperature of said exhaust gas including said target gas upstream of said catalyst in said exhaust path in response to an execution instruction to make a degradation diagnosis of said catalyst, said execution instruction being issued at an appropriate timing during said steady operation state of said internal combustion engine,
(b-2) subsequent to the measuring of the temperature of said exhaust gas in said step (b-1), injecting a fuel from said internal combustion engine to generate a gas for diagnosis,
(b-3) identifying said diagnosis index value on the basis of a time-variable profile of said electromotive force from a start to an end of exhaust of said gas for diagnosis from said catalyst, and
(b-4) diagnosing a degree of degradation in said catalyst on the basis of said diagnosis index value and a value of said threshold determined regarding the temperature of said exhaust gas measured in said step (b-1) as the temperature of said catalyst,
wherein in said step (b-4),
a diagnosis is made that degradation exceeding the acceptable degree has not occurred in said catalyst if said diagnosis index value identified in said step (b-3) is smaller than or equal to said threshold, and
a diagnosis is made that degradation exceeding the acceptable degree has occurred in said catalyst if said diagnosis index value identified in said step (b-3) is greater than said threshold.

4. The method according to claim 3, wherein a mixed-potential hydrocarbon gas sensor is used as said target gas detecting element, said mixed-potential hydrocarbon gas sensor including a sensing electrode made of a Pt—Au alloy to disable a catalytic activity in said sensing electrode.

5. A catalyst degradation diagnosis system for diagnosing a degree of degradation of a catalyst, said catalyst being provided in an exhaust path of an internal combustion engine and oxidizing or adsorbing a target gas including at least one of a hydrocarbon gas and a carbon monoxide gas contained in an exhaust gas from said internal combustion engine,
said system comprising:
a target gas detecting element configured to output an electromotive force corresponding to a concentration of said target gas as a detection signal of said target gas, said target gas detecting element being provided downstream of said catalyst in said exhaust path and sensing said target gas at said downstream side;
a control element configured to control said catalyst degradation diagnosis system; and
storage configured to hold threshold data in which a threshold determined in advance and used for diagnosing degradation of said catalyst is described in accordance with a temperature of said catalyst, wherein said internal combustion engine is configured to intentionally create a gas atmosphere for diagnosis containing a target gas having a concentration higher than a concentration of said target gas during a steady operation state of said internal combustion engine, and said control element compares a diagnosis index value with said threshold to diagnose whether degradation exceeding an acceptable degree has occurred in said catalyst, said diagnosis index value being a maximum change amount of said electromotive force after introduction of said gas atmosphere for diagnosis into said catalyst for a predetermined period of time, and said threshold being set corresponding to the temperature of said catalyst determined at a timing at which said gas atmosphere for diagnosis is introduced.

6. The system according to claim 5, wherein said target gas detecting element comprises a mixed-potential hydrocarbon gas sensor including a sensing electrode made of a Pt—Au alloy to disable a catalytic activity in said sensing electrode.

7. The system according to claim 5, further comprising:
a temperature measuring element configured to measure a temperature of said exhaust gas including said target gas upstream of said catalyst in said exhaust path in response to an execution instruction to make a degradation diagnosis of said catalyst, said execution instruction being issued from said control element at an appropriate timing at which said internal combustion engine is in said steady operation state;
an injection element configured to inject a fuel in said internal combustion engine to generate a gas for diagnosis; and
a diagnosis index value identifying element configured to identify said diagnosis index value on the basis of a time-variable profile of said electromotive force from a start to an end of a discharge of said gas for diagnosis from said catalyst, wherein subsequent to the measurement of the temperature of said exhaust gas in said temperature measuring element, said injection element injects said fuel in said internal combustion engine to generate said gas for diagnosis, and said control element is configured to
obtain a value of said threshold from said threshold data while regarding the temperature of said exhaust gas measured by said temperature measuring element as the temperature of said catalyst,
diagnose that degradation exceeding the acceptable degree has not occurred in said catalyst if said diagnosis index value identified by said diagnosis index value identifying element is smaller than or equal to said threshold, and
diagnose that degradation exceeding the acceptable degree has occurred in said catalyst if said diagnosis index value identified by said diagnosis index value identifying element is greater than said threshold.

8. The system according to claim 7, wherein said target gas detecting element comprises a mixed-potential hydrocarbon gas sensor including a sensing electrode made of a Pt—Au alloy to disable a catalytic activity in said sensing electrode.

* * * * *